(12) United States Patent
Shanbrom

(10) Patent No.: US 6,610,316 B2
(45) Date of Patent: *Aug. 26, 2003

(54) DISINFECTION BY PARTICLE-BOUND AND INSOLUBILIZED DETERGENTS

(75) Inventor: Edward Shanbrom, Santa Ana, CA (US)

(73) Assignee: Shanbrom Technologies, LLC, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/866,284

(22) Filed: May 30, 1997

(65) Prior Publication Data

US 2003/0039673 A1 Feb. 27, 2003

(51) Int. Cl.⁷ ............................................... A01N 25/26
(52) U.S. Cl. ...................... 424/417; 424/405; 424/407; 424/409; 424/418; 514/24; 514/25; 514/27; 514/642; 514/646
(58) Field of Search ................. 424/404–407, 424/409, 417, 418, 489, 493, 529–531; 514/24, 25, 27, 558, 642, 646; 535/236, 238

(56) References Cited

U.S. PATENT DOCUMENTS

| 4,839,373 A | * | 6/1989 | Ito et al. ...................... 514/367 |
| 4,841,023 A | * | 6/1989 | Horowitz ..................... 530/307 |
| 5,013,306 A | * | 5/1991 | Solomon et al. ............. 604/265 |
| 5,466,437 A | * | 11/1995 | Gaffar et al. ................. 424/52 |
| 5,869,073 A | * | 2/1999 | Sawan et al. ................ 424/406 |

* cited by examiner

Primary Examiner—Neil S. Levy
(74) Attorney, Agent, or Firm—Reed, Smith, Crosby, Heafey

(57) ABSTRACT

A detergent such as nonionic, cationic or anionic detergents and preferably a "sugar detergent" such as octyl-glucopyranoside is rendered insoluble by being bound to an inert substrate. This detergent is effective at inactivating pathogens even when so bound. Under these conditions the concentration of detergent free in solution is vanishingly low: probably below one millimolar in concentration. Addition of insoluble detergent results in effective destruction of enveloped viruses in a variety of protein containing solutions such as blood, plasma, clotting factors or other proteins purified from human blood. Because the detergent is essentially entirely bound to the solid substrate, there is little or no difficulty in ensuring that the end product is detergent-free. Because the detergent is so bound, it causes essentially no damage to proteins, blood cells and other cellular material.

12 Claims, No Drawings

DISINFECTION BY PARTICLE-BOUND AND INSOLUBILIZED DETERGENTS

BACKGROUND OF THE INVENTION

1. Field of the Invention

The field of the present invention concerns the disinfection of biological materials and in particular concerns a novel use of an insolubilized organic detergent as a disinfecting agent.

2. Description of Related Art

The present inventor has long been concerned with problems of blood borne infection. In particular, he has dealt with methods for disinfecting clotting factors and other proteins purified from blood. He has invented methods of disinfection involving iodine (see, for example, U.S. Pat. Nos. 5,360,605, and 5,370,869), and glycyrrhic triterpenoid and its derivatives (see, for example, U.S. Pat. No. 5,204,324). In addition, he was the inventor of a method of plasma protein purification employing "amphiphiles" which are more commonly known as detergents (see U.S. Pat. No. 4,314,997).

Literally amphiphile means a substance that has affinities "on both sides." This refers to a material that is both hydrophilic (dissolves readily in water) and hydrophobic (dissolves readily in organics such as lipids). Because of its dual nature, such a material can be used to dissolve or emulsify fatty organic substances into an aqueous solution as in removing dirt from clothing. Generally, a detergent is a molecule that is lipophilic (hydrophobic) at one end and hydrophilic at the other end. The hydrophilic end may be hydrophilic by virtue of charged groups, either negative (anionic) or positive (cationic) or may be hydrophilic by virtue of polar but uncharged (nonionic) groups such as hydroxyl groups or oxygen atoms.

This dual hydrophobic/hydrophilic nature gives detergents or amphiphiles favorable properties in purification of therapeutic blood proteins although they may also denature proteins. Blood proteins can be contaminated with any of a number of disease organisms including viruses causing AIDS and hepatitis. Many important disease-causing viruses are composed of a nucleic acid core surrounded by a lipid membrane. It has been shown that detergents can be effective at inactivating viruses. It seems likely that this is due to the detergent emulsifying or otherwise disrupting lipid structures essential for viral activity. One real problem with detergents is that they are also capable of disrupting other vital lipid-based structures like the biomembranes that surrounds and form a significant internal structural component of every animal and plant cell. It turns out to be difficult to find detergents that are sufficiently active to disrupt infective agents while being gentle enough to spare living cells. As a result, huge numbers of detergent structures have been screened looking for optimal detergents. U.S. Pat. No. 4,314,997, mentioned above, gives a lengthy list of candidate detergents.

At the risk of simplifying a hugely complex area it can be considered that ionic detergents (either anionic or cationic) are the most active, and while being very effective at destroying viruses, may readily destroy or damage living cells. Generally, one way to overcome cell destruction is to lower the working concentration of the detergent. However, it is often the case that when the detergent concentration is sufficiently lowered to avoid cell damage, it is also too low to destroy viruses.

The nonionic (uncharged) detergents are generally less active at destroying or damaging cells. Hence it may be possible to find concentrations of nonionic detergents that destroy virus without excessively damaging cells. However, because these detergents are relatively less active, rather high concentrations of detergent are required to adequately destroy viruses. For example, U.S. Pat. No. 4,314,997 claims the broad concentration range of 0.25% to 10% by weight of a variety of detergents. However, the preferred concentration of one nonionic detergent, Triton X-100 (t-octylphenoxypolyethoxyethanol),is at least 2%, while other procedures may use even higher concentrations of detergent. It should be apparent that this may be a case of trading one difficulty for another. Triton X-100, like most detergents, is extremely harmful when injected intravenously. Therefore, removing detergents after they are used for disinfection becomes a very real and significant problem. This problem is merely exacerbated where an extremely high concentration of detergent is used, and especially when one considers that micellar characteristics make it difficult to remove Triton X-100 by dialysis.

One popular method of disinfecting blood products is the so-called "solvent detergent" process. In this process plasma viruses are inactivated by the addition of relatively high concentrations of detergents together with an organic solvent-tri-n-butyl-phosphate. The detergent and solvent are then removed by partitioning the protein solution against an organic liquid. The detergent and solvent partition into this liquid and are, hence, eliminated. Most often bland organic liquids such as castor or soy bean oil are used. The oil is then removed by hydrophobic chromatography. It is not difficult to imagine the time and expense of partitioning the plasma and of regenerating or replacing the chromatographic components. Therefore, there remains a significant need for a disinfecting method with the advantages of detergents but which the usual problems of detergent removal.

OBJECTS AND SUMMARY OF THE INVENTION

It is an object of the present invention to provide an improved detergent-based method for inactivation of disease-causing organisms;

It is a further object of the present invention to provide an inactivation method which uses detergent in an easily removable form;

It is an additional object of the present invention to provide a novel disinfecting reagent in the form of a complex between a detergent and a detergent-binding material.

These and other objects are met in an inactivation method that employs a detergent such as nonionic, cationic or anionic detergents and preferably a "sugar detergent" such as octyl-glucopyranoside. This detergent is effective at inactivating pathogens even when bound by a solid support. Under these conditions the concentration of detergent free in solution is vanishingly low: probably well below one millimolar in concentration. Addition of insoluble detergent results in effective destruction of enveloped viruses in a variety of protein-containing solutions such as clotting factors or other proteins purified from human blood. Because the detergent is essentially entirely bound to a solid substrate, there is little or no difficulty in ensuring that the end product is detergent-free. Because the detergent is so bound, it causes essentially no damage to proteins, blood cells and other cellular material.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved way of disinfecting plasma and plasma proteins and other protein solutions by the use of insoluble detergents bound to organic polymers such as polystyrene.

While the present invention is functional with a wide variety of detergents including anionic detergents such as cholic and deoxycholic acids (bile acids), cationic detergents such as benzalkonium chloride, and nonionic detergents such as Triton X-100, the present inventor has discovered that surprisingly low concentrations of n-octyl-B-D-glucopyranoside (OG) are especially effective in viral and other pathogen inactivation. Levels of about 0.03% are effective at inactivating some viruses even in the presence of plasma proteins. This discovery forms the basis of copending application Ser. No. 08/785,984. This concentration of detergents represents the lower edge of the concentration range claimed in the prior art and represents an amount of detergent far below that actually used to disinfect plasma and plasma products. OG is a nonionic detergent, one of the "sugar detergents" so-called because its molecular structure consists of a sugar (glucose unit or glucopyranoside) with an attached straight carbon (octyl) chain. The numerous hydroxyl groups of the sugar provide the hydrophilic part of the detergent while the aliphatic carbon chain is strongly hydrophobic. A number of other analogous sugar detergents are currently known wherein the glucose group is replaced by other sugars or disaccharides while the aliphatic carbon chain is replaced by straight or branched aliphatic chains of various lengths. OG, insolubilized according to the present invention, has proven to be especially effective. Although OG is currently preferred, closely related sugar detergents based on mono or disaccharides with aliphatic chains of between 6 and 14 carbons are usable in the present invention. Some of the other sugar include: n-decanoylsucrose, n-decyl-β-D-glucopyranoside, n-decyl-β-D-maltopyranoside, n-dodecanoylsucrose, n-dodecyl-β-D-glucopyranoside, n-dodecyl-β-D-maltopyranoside, heptyl-β-D-glucopyranoside, heptyl-β-D-thioglucopyranoside, n-hexyl-β-D-glucopy-ranoside, n-nonyl-β-D-glucopyranoside, n-octanoylsucrose, n-octyl-β-D-glucopyranoside, n-octyl-β-D-maltopyranoside, and n-octyl-β-D-thioglucopyranoside.

Experiment #1: Lytic Effect of Insoluble Detergent on Whole Blood

It is important that any treatment intended to inactivate microbes shows no adverse effects on proteins and cells. It is well-known that detergents can damage biomembranes. This is most readily seen in the case of red blood cells (RBC) where any membrane damage is readily visible as leakage of hemoglobin (hemolysis).

Two mL of Calbiosorb resin (plastic resin beads designed to absorb detergents from aqueous solutions) were placed in a conical centrifuge tube and dispersed in 10 mL of 5 mM OG dissolved in phosphate buffered saline (PBS). The resulting suspension was mixed for 30 min to ensure complete absorption of the OG. The beads were allowed to settle and the supernatant PBS removed by aspiration. When the supernatant PBS was shaken in a sealed tube, it showed essentially no foaming indicating that all of the OG had been absorbed by the resin.

Five mL of fresh whole blood were added to the tube containing the detergent-laden resin, and the tube was mixed until the resin was completely suspended in the blood. After 5 min incubation at room temperature, the tube was centrifuged at 2,000 rpm for 5 min. The centrifugation process caused the contents of the tube to separate into three distinct layers: red cell pellet at the bottom, plasma above the red cells, and beads floating on top of the plasma.

There was no hemolysis immediately visible indicating that the OG was so strongly bound to the resin that it was unable to affect the blood cell membranes. Over a ten day period the resin gradually sank into the plasma and eventually formed a layer above the red cells. After several days, there was some indication of hemolysis, but untreated cells also show limited hemolysis after several days. In any case this experiment indicates that a brief treatment with insoluble detergent (i.e., one day or less) causes no apparent harm to the blood cells.

Experiment #2: Anti-Viral and Lytic Effect of Insoluble Detergent on Whole Blood Two 10 mL aliquots of 5 mM OG and two 10 mL aliquots of 10 mM OG were prepared in distilled water. Each aliquot was added to 20 mL of Calbiosorb resin and the resin-OG mixture was incubated for 60 min at room temperature with occasional mixing to ensure uptake of the detergent by the resin.

Twenty five mL of whole blood (EDTA anticoagulated) was obtained via venipuncture of the inventor. To 20 mL of this blood 0.4 mL of a stock vesicular stomatitis virus (VSV) suspension was added (spiked blood). A similar amount of VSV was also added to 20 mL of cell culture solution to act as a medium control. This virus is a good model for easily inactivated enveloped viruses The supernatant from the resin incubation was decanted and 10 mL of spiked blood was added to one 5 mM batch of resin and to one 10 mM batch of resin. The medium control was treated in the same manner. The tubes were incubated at room temperature for 24 hr with samples taken at 60 min and 24 hr. The samples were analyzed by a virus end point assay (VEPA) and the titered results shown in Table 1.

TABLE 1

|  | 1 | 2 | 3 | 4 | 5 | 6 | 7 | 8 | 9 | 10 | 11 | 12 | 13 | 14 | 15 | Titer |
| --- | --- | --- | --- | --- | --- | --- | --- | --- | --- | --- | --- | --- | --- | --- | --- | --- |
| whole blood control | 4 | 4 | 4 | 4 | 4 | 4 | 4 | 4 | 4 | 4 | 4 | 4 | 4 | 2 | 0 | 9.8 |
| whole blood 5 mM 60 min | 4 | 4 | 4 | 4 | 4 | 4 | 4 | 4 | 4 | 4 | 4 | 4 | 4 | 2 | 0 | 10.0 |

TABLE 1-continued

| | 1 | 2 | 3 | 4 | 5 | 6 | 7 | 8 | 9 | 10 | 11 | 12 | 13 | 14 | 15 | Titer |
|---|---|---|---|---|---|---|---|---|---|---|---|---|---|---|---|---|
| whole blood 5 mM 24 hr | 4 | 4 | 4 | 4 | 4 | 4 | 4 | 4 | 4 | 4 | 4 | 4 | 1 | 0 | 0 | 8.9 |
| whole blood 10 mM 60 min | 4 | 4 | 4 | 4 | 4 | 4 | 4 | 4 | 4 | 4 | 4 | 4 | 4 | 2 | 0 | 9.8 |
| whole blood 10 mM 24 hr | 4 | 4 | 4 | 4 | 4 | 4 | 4 | 4 | 4 | 4 | 4 | 4 | 0 | 0 | 0 | 8.7 |
| Medium control | 4 | 4 | 4 | 4 | 4 | 4 | 4 | 4 | 4 | 4 | 4 | 4 | 4 | 2 | 0 | 9.8 |
| Medium 5 mM 60 min | 4 | 4 | 4 | 4 | 4 | 4 | 4 | 4 | 4 | 4 | 4 | 4 | 4 | 2 | 0 | 9.8 |
| Medium 5 mM 24 hr | 4 | 4 | 4 | 4 | 4 | 4 | 4 | 4 | 4 | 1 | 0 | 0 | 0 | 0 | 0 | 6.8 |
| Medium 10 mM 60 min | 4 | 4 | 4 | 4 | 4 | 4 | 4 | 4 | 4 | 4 | 4 | 4 | 4 | 3 | 0 | 10.0 |
| Medium 10 mM 24 hr | 4 | 4 | 4 | 4 | 4 | 4 | 2 | 0 | 0 | 0 | 0 | 0 | 0 | 0 | 0 | 4.9 |

There was no evidence of hemolysis. This experiment indicates that the detergent is very tightly bound and is able to attack the virus only very slowly. This suggests that higher detergent:bead ratios may be more effective by saturating the resin and allowing a more rapid anti-viral effect.

Experiment #2: Higher Ratio Insoluble Detergent Inactivation of Vesicular Stomatitis (VSV) Virus This experiment was carried out like the immediately previous experiment except that 0 mM (control), 10 mM, 25 mM, 50 mM, and 100 mM OG solutions were prepared in distilled water. Ten mL of each solution was added to 2 mL of Calbiosorb resin and incubated for 60 min as before. The supernatant from each tube was decanted and shaken to observe any foaming as an indication of free detergent. Only the 100 mM sample showed any free detergent indicating that the beads were saturated (or that 60 min incubation is insufficient for complete detergent binding).

To each aliquot of insoluble detergent-beads 10 mL of VSV-spiked whole blood was added. The blood and beads were mixed and incubated for 60 min at room temperature and then centrifuged to pellet the cells. There was no sign of hemolysis in any of the treatments. Samples were then taken for VEPA analysis as before. The tubes were mixed to resuspend the cells and resin. A second sample was taken at 24 hr and a third at 48 hr. No hemolysis was apparent at any time. The results are given in Table 2.

Interestingly, the resin density was affected by the detergent concentration. In the 10 mM, 25 mM and 50 mM samples the resin was at the top of the plasma after 30 min, but after about 90 min the resin had settled onto the red cell layer. In the 100 mM sample, the resin did not separate and the red cells did not pellet cleanly until after 4 hr had passed.

TABLE 2

| | Dilution: | 1 | 2 | 3 | 4 | 5 | 6 | 7 | 8 | 9 | 10 | 11 | 12 | 13 | 14 | 15 | Titer |
|---|---|---|---|---|---|---|---|---|---|---|---|---|---|---|---|---|---|
| 60 min | 0 mM (control) | 4 | 4 | 4 | 4 | 4 | 4 | 4 | 4 | 4 | 4 | 4 | 4 | 4 | 2 | 0 | 9.8 |
| | 10 mM | 4 | 4 | 4 | 4 | 4 | 4 | 4 | 4 | 4 | 4 | 4 | 4 | 4 | 2 | 0 | 9.8 |
| | 25 mM | 4 | 4 | 4 | 4 | 4 | 4 | 4 | 4 | 4 | 4 | 4 | 4 | 4 | 1 | 0 | 9.6 |
| | 50 mM | 4 | 4 | 4 | 4 | 4 | 4 | 4 | 4 | 4 | 4 | 1 | 0 | 0 | 0 | 0 | 7.5 |
| | 100 mM | 4 | 4 | 4 | 4 | 4 | 4 | 4 | 4 | 4 | 0 | 0 | 0 | 0 | 0 | 0 | 6.6 |
| 24 hr | 0 mM (control) | 4 | 4 | 4 | 4 | 4 | 4 | 4 | 4 | 4 | 4 | 4 | 4 | 4 | 2 | 0 | 9.8 |
| | 10 mM | 4 | 4 | 4 | 4 | 4 | 4 | 4 | 4 | 4 | 4 | 4 | 4 | 4 | 0 | 0 | 9.5 |
| | 25 mM | 4 | 4 | 4 | 4 | 4 | 4 | 4 | 4 | 4 | 4 | 3 | 0 | 0 | 0 | 0 | 7.9 |
| | 50 mM | 4 | 4 | 4 | 4 | 4 | 4 | 4 | 4 | 0 | 0 | 0 | 0 | 0 | 0 | 0 | 5.9 |
| | 100 mM | 4 | 4 | 4 | 4 | 4 | 4 | 2 | 0 | 0 | 0 | 0 | 0 | 0 | 0 | 0 | 3.5 |
| 48 hr | 0 mM (control) | 4 | 4 | 4 | 4 | 4 | 4 | 4 | 4 | 4 | 4 | 4 | 4 | 4 | 2 | 0 | 9.8 |
| | 10 mM | 4 | 4 | 4 | 4 | 4 | 4 | 4 | 4 | 4 | 4 | 4 | 4 | 4 | 0 | 0 | 9.5 |
| | 25 mM | 4 | 4 | 4 | 4 | 4 | 4 | 4 | 4 | 4 | 1 | 0 | 0 | 0 | 0 | 0 | 6.7 |
| | 50 mM | 4 | 4 | 4 | 4 | 4 | 4 | 2 | 0 | 0 | 0 | 0 | 0 | 0 | 0 | 0 | 3.5 |
| | 100 mM | 4 | 4 | 4 | 0 | 0 | 0 | 0 | 0 | 0 | 0 | 0 | 0 | 0 | 0 | 0 | 2.4 |

These results indicate that insoluble detergent can effectively destroy VSV even in the presence of whole blood. It would appear that the ratio of detergent to resin is critical. Higher amounts of detergent per amount of resin may increase the amount of reactive detergent or may result in somewhat weaker binding of detergent. On the other hand increasing the overall amount of resin may increase the reactive surface area and may also play a critical role in determining the optimal detergent/resin ratio.

Experiment #3: Inactivation of Bovine Viral Diarrhea (BVD) Virus

This experiment was designed to test the effectiveness of insoluble detergent on inactivating BVD, an enveloped virus and a good model for other thick enveloped viruses such as HCV. The experiment was carried out exactly as Experiment #2, above. The results are shown in Table 3.

TABLE 3

|  | Dilution: | 1 | 2 | 3 | 4 | 5 | 6 | 7 | 8 | 9 | 10 | 11 | 12 | Titer |
|---|---|---|---|---|---|---|---|---|---|---|---|---|---|---|
| 60 min | 0 mM (control) | 4 | 4 | 4 | 4 | 4 | 4 | 1 | 0 | 0 | 0 | 0 | 0 | 4.6 |
|  | 10 mM | 4 | 4 | 4 | 4 | 4 | 4 | 0 | 0 | 0 | 0 | 0 | 0 | 4.5 |
|  | 25 mM | 4 | 4 | 4 | 4 | 4 | 4 | 2 | 0 | 0 | 0 | 0 | 0 | 4.9 |
|  | 50 mM | 4 | 4 | 4 | 4 | 4 | 4 | 1 | 0 | 0 | 0 | 0 | 0 | 4.6 |
|  | 100 mM | 4 | 4 | 4 | 4 | 4 | 4 | 1 | 0 | 0 | 0 | 0 | 0 | 4.6 |
| 24 hr | 0 mM (control) | 4 | 4 | 4 | 4 | 4 | 4 | 2 | 0 | 0 | 0 | 0 | 0 | 4.9 |
|  | 10 mM | 4 | 4 | 4 | 4 | 4 | 4 | 1 | 0 | 0 | 0 | 0 | 0 | 4.6 |
|  | 25 mM | 4 | 4 | 4 | 4 | 4 | 4 | 0 | 0 | 0 | 0 | 0 | 0 | 4.5 |
|  | 50 mM | 4 | 4 | 4 | 4 | 4 | 4 | 0 | 0 | 0 | 0 | 0 | 0 | 4.5 |
|  | 100 mM | 4 | 4 | 4 | 4 | 4 | 2 | 0 | 0 | 0 | 0 | 0 | 0 | 4.6 |
| 24 hr | 0 mM (control) | 4 | 4 | 4 | 4 | 4 | 4 | 1 | 0 | 0 | 0 | 0 | 0 | 4.6 |
|  | 10 mM | 4 | 4 | 4 | 4 | 4 | 4 | 1 | 0 | 0 | 0 | 0 | 0 | 4.6 |
|  | 25 mM | 4 | 4 | 4 | 4 | 4 | 4 | 0 | 0 | 0 | 0 | 0 | 0 | 4.5 |
|  | 50 mM | 4 | 4 | 4 | 4 | 4 | 0 | 0 | 0 | 0 | 0 | 0 | 0 | 3.8 |
|  | 100 mM | 4 | 4 | 4 | 0 | 0 | 0 | 0 | 0 | 0 | 0 | 0 | 0 | 2.5 |

These results indicate that like VSV BVD can be killed by insoluble detergent. However, BVD is more resistant than VSV and clearly responds better to higher detergent/resin ratios.

Experiment #4: Effect of Increasing Available Surface Area of Resin

In this experiment a 100 mM solution of OG in distilled water was prepared. This time twice the volume (i.e., twice the reactive surface area) of resin (4 mL) was added and the mixture treated as above. There was no evidence of foam in the supernatant indicating that all of the detergent was bound by the resin. The insoluble detergent-beads were added to 10 mL of BVD-spiked blood as in the immediately previous experiment. Again, samples were taken at 60 min, 24 hr and 48 hr. This time, as shown in Table 4, the viral killing was significantly improved suggesting that having an increased surface area to present insoluble detergent to the contaminated blood results in improved results. There was no apparent increase in hemolysis as might be expected if this effect were caused by some increase in the concentration of unbound (solubilized) detergent.

TABLE 4

|  | 1 | 2 | 3 | 4 | 5 | 6 | 7 | 8 | 9 | 10 | 11 | 1'2 | Titer |
|---|---|---|---|---|---|---|---|---|---|---|---|---|---|
| Control | 4 | 4 | 4 | 4 | 4 | 4 | 1 | 0 | 0 | 0 | 0 | 0 | 4.7 |
| 60 min | 4 | 4 | 4 | 4 | 0 | 0 | 0 | 0 | 0 | 0 | 0 | 0 | 3.1 |

TABLE 4-continued

|  | 1 | 2 | 3 | 4 | 5 | 6 | 7 | 8 | 9 | 10 | 11 | 1'2 | Titer |
|---|---|---|---|---|---|---|---|---|---|---|---|---|---|
| 24 hr | 4 | 0 | 0 | 0 | 0 | 0 | 0 | 0 | 0 | 0 | 0 | 0 | 1.0 |
| 48 hr | 0 | 0 | 0 | 0 | 0 | 0 | 0 | 0 | 0 | 0 | 0 | 0 | 0 |

Table 5 shows the same experiment repeated using hydrophobic resin sold by Bio-Rad (BioBeads SM2, Catalog #152-3920) The results are essentially identical indicating that the source of hydrophobic resin is not critical.

TABLE 5

|  | 1 | 2 | 3 | 4 | 5 | 6 | 7 | 8 | 9 | 10 | 11 | 1'2 | Titer |
|---|---|---|---|---|---|---|---|---|---|---|---|---|---|
| Control | 4 | 4 | 4 | 4 | 4 | 4 | 2 | 0 | 0 | 0 | 0 | 0 | 4.9 |
| 60 min | 4 | 4 | 4 | 3 | 0 | 0 | 0 | 0 | 0 | 0 | 0 | 0 | 3.0 |
| 24 hr | 4 | 1 | 0 | 0 | 0 | 0 | 0 | 0 | 0 | 0 | 0 | 0 | 1.1 |
| 48 hr | 0 | 0 | 0 | 0 | 0 | 0 | 0 | 0 | 0 | 0 | 0 | 0 | 0 |

Experiment #5. Insoluble Triton X-100

Calbiosorb resin has an extremely high affinity for Triton x-100. Therefore, insoluble Triton X-100 was prepared in a manner identical to that used for insoluble OG. The material was prepared using the proportions of 10 mL of 100 mM Triton X-100 added to 2 mL of the resin. After absorption of the detergent, the resin was removed from the supernatant as explained above under Experiment #2.

In an initial experiment 10 mL of whole blood was added to a tube containing 4.0 mL of the Triton-resin. The tube was mixed thoroughly and observed for hemolysis over a seven day period. There was no signs of hemolysis although addition of a similar amount of soluble Triton results in immediate hemolysis.

Ten mL of VSV spiked plasma (prepared as explained above) was added to a second tube containing 4.0 mL of Triton-resin. The tube was mixed for 60 min at room temperature and a sample was taken and analyzed by a viral end point assay. Results of the assay are shown in Table 6.

TABLE 6

|  | 1 | 2 | 3 | 4 | 5 | 6 | 7 | 8 | 9 | 10 | 11 | 12 | 13 | 14 | 15 | Titer |
|---|---|---|---|---|---|---|---|---|---|---|---|---|---|---|---|---|
| Control | 4 | 4 | 4 | 4 | 4 | 4 | 4 | 4 | 4 | 4 | 4 | 2 | 0 | 0 | 0 | 4.7 |
| 60 min | 4 | 4 | 4 | 4 | 4 | 1 | 0 | 0 | 0 | 0 | 0 | 0 | 0 | 0 | 0 | 3.1 |

These results show that while Triton-resin is somewhat less effective against virus than the comparable OG-resin, there must be extremely avid binding of the detergent since there is no sign of hemolysis. This suggests that even higher levels of Triton-resin could be used to increase the virucidal effect without resulting in cell damage.

Experiment #6: Binding of Additional Detergents

The above results can be readily extended to a wide range of detergents and resins. It is anticipated that certain detergents will prove to be more effective than others as disinfectants. Similarly some resins may prove more effective at binding particular detergents. Besides the simple hydrophobic-binding resin (e.g. specially prepared polystyrene), ion exchange resins appear to be especially effective at binding charged detergents. As expected, anion exchange resins effectively bind anionic detergents while cation exchange resins bind cationic detergents. In the case of ion exchange resins it is likely that two-fold binding takes place. The charged end of the detergent is bound by the ion exchange group while the lipophilic end of the detergent is bound by the hydrophobic matrix of the exchange resin. In this experiment 10 mM solutions of a number of detergents were made. Three non-polar (non-ionic) detergents (OG, Triton X-100 and Tween-20) were tested; two zwitterionic detergents (CHAPS (3-[(3-Chloramidopropyl)-dimethylammonio]-1-propanesulfanate) and CHAPSO, (3-[(3-Chloramidopropyl)-dimethylammonio]-2-hydroxyl 1-propanesulfanate), CalBiochem) were tested; five anionic detergents (caprylic acid, cholic acid, deoxycholic acid, sodium dodecylsulfate (SDS), and dioctyl sulfosuccinate (DSS)) were tested; and two cationic detergents (benzalkonium chloride (BC), and tetradecyltrimethylammonium bromide (TTAB)) were tested. It should be noted that cationic detergents of this type (quaternary ammonium salts) are noted for their germicidal properties. Binding to Calbiosorb (hydrophobic resin), Purolite (anion exchange resin) and polystyrene was tested. After incubating the detergent solution with the resin beads, the beads were removed and the supernatant examined for foaming presence (+) or absence (−) as an indicator of detergent presence as shown in Table 7.

TABLE 7

| Detergent | Type | Calbiosorb | Polystyrene | Purolite |
|---|---|---|---|---|
| OG | nonionic | − | + | + |
| Triton X-100 | nonionic | − | + | + |
| Tween-20 | nonionic | − | + | + |
| CHAPS | zwitterionic | − | + | +/− |
| CHAPSO | zwitterionic | − | + | +/− |
| Caprylate | anionic | − | + | − |
| Cholate | anionic | − | + | − |
| Deoxycholate | anionic | − | + | − |
| SDS | anionic | − | + | − |
| DSS | anionic | − | + | − |
| BC | cationic | − | + | +/− |
| TTAB | cationic | − | + | +/− |

These results show that, as expected, Calbiosorb is very good at binding a wide range of detergents. Although polystyrene would be expected to bind detergents by hydrophobic interactions, it was relatively ineffective in these experiments probably because the solid polystyrene beads used had insufficient surface area. The anion exchange resin was somewhat effective in binding anionic detergents. The binding of bile salt detergents (cholate and deoxycholate) is particularly interesting because these are natural biological detergents and would be expected to be safe and nontoxic. Preliminary experiments with cholestyramine resin as an insoluble binding agent for these materials have shown beneficial detergent effects (e.g. disruption of pathogens) with bound bile salts.

The experiments detailed herein disclose the unexpected discovery that detergent molecules bound to solid materials remain effective in destroying pathogens such as viruses. Hitherto this discovery it was thought necessary to add disinfecting concentrations (often very high) of detergent to a liquid to be disinfected. After sufficient incubation to maximally inactivate the pathogens, the detergent was removed by chromatography or by solvent extraction. In any case the incubation in high concentrations of detergent would damage or lyse cells making this type of pathogen inactivation inappropriate for liquids containing cells or cellular components (e.g., blood). Furthermore, the removal of detergent was often laborious, costly and often resulted in additional damage to the liquid being treated. Because traces of detergent are often very toxic these methods are generally inappropriate for vaccines or other injectable substances.

Experiment #6: Bound Detergents as Intermediates

The fact that insoluble or bound detergents maintain many of the beneficial properties of the soluble material suggests that other insoluble substances might also exert useful effects. There are a number of germicidal or disinfectant molecules that are essentially insoluble. Typical is the germicide known as triclosan. This chlorinated material is essentially insoluble in water but is soluble in organic solvents and lipids. It is commonly used as a disinfectant additive in soaps and the like. Triclocarban is a similar material. Parabens (including methyl paraben) are water insoluble germicides used in cosmetics and like applications.

A 0.3% solution of triclosan was made in an aqueous solution of 2% Triton X-100. The normally insoluble triclosan was slowly dissolved under these conditions. Addition of triclosan to Triton X-100 appears to potentiate the antiviral effectiveness of the detergent. In one experiment a 100 mM solution of triclosan was made in 2% aqueous Triton X-100. Five mL of this material was added to 50 mL of plasma spike with EMC virus and incubated for 60 min at room temperature. Results of viral end point assay are shown in Table 8. The test material completely eliminated the virus. Triton alone is virucidal, but 0.2% Triton is not nearly effective as Triton plus triclosan.

TABLE 8

| Dilution | 1 | 2 | 3 | 4 | 5 | 6 | 7 | 8 | 9 | 10 | 11 | 12 | Titer |
|---|---|---|---|---|---|---|---|---|---|---|---|---|---|
| Control | 4 | 4 | 4 | 4 | 4 | 4 | 4 | 2 | 0 | 0 | 0 | 0 | 5.6 |
| Triclosan | 0 | 0 | 0 | 0 | 0 | 0 | 0 | 0 | 0 | 0 | 0 | 0 | 0 |

Experiments then were undertaken which demonstrated that treating detergent absorbing beads either with triclosan-Triton solution or directly with finely divided triclosan resulted in the uptake of triclosan by the beads. When these beads were tested in viral assays in a manner similar to the insoluble detergent beads, they showed enhanced viral kill over detergent alone beads. At this time it appears that a combination of triclosan and detergent is superior to either component alone. It is hypothesized that the bound detergent somehow mobilizes the triclosan and makes it more available for killing. In any case the soluble concentrations of either detergent or triclosan (i.e., the actual amount in solution) is very low. These results strongly suggest that the combination of other hydrophobic, insoluble germicides and disinfectants (such as triclocarban and parabens) with detergents on a binding support would also be effective.

The present method employing insoluble detergents avoids most of the problems of the prior art. When the detergent is bound to an inert binding material such as polystyrene or polystyrene-based ion exchange resins, the concentration of detergent present in the solution is extremely low: too low to cause discernible foaming and too low to cause cell damage. Nevertheless, there is sufficient detergent to effectively inactivate pathogens. This result may seem counterintuitive. Without wishing to be held to any one explanation of the present invention the inventor suggests that the inactivation process may occur when virus or other pathogens come into physical contact with the detergent bound to the surface of the binding material. Since the detergent is unable to leave the binding material, it cannot accumulate in cellular membranes and damage them. The insoluble detergents of the present invention are ideal for inactivating pathogens in blood, blood fractions, other biologicals (e.g., antibodies and vaccines) as well as any other liquids where presence of pathogens is of concern such as liquid foods and beverages. The materials can be applied in a batch process where the insoluble detergents are mixed with the target liquid to effect pathogen inactivation. In the alternative, flow through methods (e.g. chromatographic methods) can be used where the target liquid is allowed to percolate through a bed or column of the insoluble detergent. In either case the quantity of insoluble detergent and the contact time can be readily adjusted to provide optimal inactivation of pathogens.

The current process has been demonstrated with a variety of detergents, and while sugar detergents are currently preferred, a wide variety of detergent molecules including charged (anionic, cationic, and zwitterionic) and noncharged (nonionic or nonpolar) detergents are suitable. The inert binding material can be any of a variety of substances. Currently polystyrene resins and similar plastics that bind detergent primarily through hydrophobic and van der Waal's interactions are preferred. Specially prepared materials result in enhanced detergent binding. Obviously other similar materials that bind detergent are within the contemplation of the present invention. In addition, charged detergents can be bound effectively by the appropriate ion exchange resin where binding is both by ionic interaction through the ion exchange group as well as hyrophobic through the bulk material of the resin.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention.

What is claimed is:

1. A process for inactivating pathogens in an aqueous liquid comprising the steps of contacting the aqueous liquid with a volume of plastic resin particles to which has been bound a detergent selected from the group consisting of a sugar detergent, t-octylphenoxypolyethanol, dioctyl sulfosuccinate, polyoxyethylenesorbitan, (3-[(3-cholamidopropyl) dimethylammonio]-1-propane sulfonate), (3-[(3-cholamidopropyl) dimethylammonio]-2-hydroxy-1-propane sulfonate), cholate and deoxycholate, and then removing the aqueous liquid from contact with the plastic resin particles.

2. The process of claim 1, further comprising the step of binding a water insoluble germicidal agent to the plastic resin particles prior to contacting the aqueous liquid with said particles.

3. The process of claim 2, wherein the water insoluble germicidal agent is selected from the group consisting of triclosan, triclocarban and parabens.

4. The process of claim 1, wherein the plastic resin beads are made of polystyrene.

5. The process of claim 1, wherein the sugar detergent is selected from the group consisting of octyl-glucopyranoside, n-decanoylsucrose, n-decyl-β-D-glucopyranoside, n-decyl-β-D-maltopyranoside, n-dodecanoylsucrose, n-dodecyl-β-D-glucopyrafloside, n-dodecyl-β-D-maltopyranoside, heptyl-β-D-glucopyranoside, heptyl-β-D-thioglucopyranoside, n-hexyl-β-D-glucopy-ranoside, n-nonyl-β-D-glucopyranoside, n-octanoylsucrose, n-octyl-β-D-glucopy-ranoside, n-octyl-β-D-maltopyranoside, and n-octyl-β-D-thioglucopyranoside.

6. A process for inactivating pathogens in blood or an aqueous liquid containing blood cells without damaging the blood cells comprising the steps of:

contacting a quantity of plastic resin particles with a solution of a sugar detergent and allowing the sugar detergent to bind to the plastic resin particles;

removing the now detergent-containing plastic resin particles from the solution;

contacting blood or an aqueous liquid containing blood cells with the detergent containing plastic resin particles;

continuing the contact of the detergent-containing plastic resin particles and the blood or aqueous liquid containing blood cells for sufficient time to allow pathogen inactivation without damaging the blood cells; and removing the blood or aqueous liquid from contact with the plastic resin particles, whereby pathogens are inactivated without damaging the blood cells.

7. The process of Claim 6, wherein the sugar detergent is selected from the group consisting of octyl-glucopyranoside, n-decanoylsucrose, n-decyl-β-D-glucopyranoside, n-decyl-β-D-maltopyranoside, n-dodecanoylsucrose, n-dodecyl-β-D-glucopyranoside, n-dodecyl-β-D-maltopyranoside, heptyl-β-D-glucopyranoside, heptyl-β-D-thioglucopyranoside, n-hexyl-β-D-glucopy-ranoside, n-nonyl-β-D-glucopyranoside, n-octanoylsucrose, n-octyl-β-D-glucopy-ranoside, n-octyl-β-D-maltopyranoside, and n-octyl-β-D-thioglucopyranoside.

8. The process of claim 6, wherein a water insoluble germicidal agent is added to the detergent solution.

9. The process of claim 8, wherein the water insoluble germicidal agent is selected from the group consisting of triclosan, triclocarban and parabens.

10. The process of claim 6, wherein the plastic resin beads are made of polystyrene.

11. A process for inactivating pathogens in blood or an aqueous liquid containing blood cells without damaging the blood cells comprising the steps of:

binding a sugar detergent selected from the group consisting of octyl glucopyranoside, n-decanoylsucrose, n-decyl-β-D-glucopyranoside, n-decyl-β-D-maltopyranoside, n-dodecanoylsucrose, nβdodecyl-β-D-glucopyranoside, dodecyl-β-D-maltopyranoside, heptyl-β-D-glucopyranoside, heptyl-β-D-thioglucopyranoside, n-hexyl-β-D-glucopy-ranoside, n-nonyl-β-D-glucopyranoside, n-octanoylsucrose, n-octyl-β-D-glucopy-ranoside, n-octyl-β-D-maltopyranOside, and n-octyl-β-D-thioglucopyranoside to plastic resin particles that bind detergent to form detergent containing plastic resin particles;

contacting blood or an aqueous liquid containing blood cells with the detergent containing plastic resin particles;

continuing the contact between the detergent-containing plastic resin particles and the blood or aqueous liquid containing blood cells for sufficient time to allow pathogen inactivation; and removing said liquid from contact with the plastic resin particles.

12. The process of claim 11, wherein the plastic resin beads are made of polystyrene.

* * * * *